United States Patent [19]

Sawyer et al.

[11] Patent Number: 5,281,611

[45] Date of Patent: Jan. 25, 1994

[54] EUTHANASIA COMPOSITIONS

[75] Inventors: Donald C. Sawyer, Okemos; Theodore M. Brody, East Lansing; Marlee A. Langham, DeWitt, all of Mich.

[73] Assignee: Board of Trustees operating Michigan State University, East Lansing, Mich.

[21] Appl. No.: 631,090

[22] Filed: Dec. 19, 1990

[51] Int. Cl.⁵ .................. A61K 31/44; A61K 31/47; A61K 31/16
[52] U.S. Cl. .................................. 514/297; 514/313; 514/625; 514/629
[58] Field of Search ............... 514/296, 313, 629, 630, 514/297, 625

[56] References Cited
PUBLICATIONS

CA 86(4):21733g, Fed. Regis., 41(201), 45547, Oct. 15, 1976.
Dialog Acc. No.: 00050539, Drug Name: Chloroquine; Jaeger et al., Med-Toxicol 2/4 (242-273) 1987.
Diagol Acc. No.: 01999557, American Hospital Formulary Service; Monography Title: Quinacrine Hydrochloride, 1990.
Don Michael et al., Am. Heart J., 79(6), 1970, pp. 831-842.
Mudge, G. H., Potassium section VII, Water, Salts and Ions. In The Pharm. Basis of Therapeutics, Goodman and Gilman, Eds., MacMillan Publishing Co., New York, 1985, pp. 866-874.
Tona, Lutete, et al., European Journal of Pharmacology, 178, 293-301 (1990).

Primary Examiner—Frederick E. Waddell
Assistant Examiner—Kimberly R. Jordan
Attorney, Agent, or Firm—Ian C. McLeod

[57] ABSTRACT

An euthanasia solution based upon gamma-hydroxybutramide and a cardiotoxic amount of a compound selected from chloroquine and quinacrine is described. The composition provides effective euthanasia without unwanted side effects.

23 Claims, No Drawings

EUTHANASIA COMPOSITIONS

BACKGROUND OF THE INVENTION (1) Field of the Invention

The present invention relates to euthanasia compositions which are used for producing humane death in lower mammals. In particular the present invention relates to euthanasia solutions which use the anesthetic gamma-hydroxybutramide (embutramide) as a basis for formulating the composition. (2) Prior Art Euthanasia compositions for lower mammals are necessary in order to provide humane death. Generally the solutions are injected intravenously or intraperitoneally. Users of such solutions are animal shelters, humane societies, veterinarians, veterinary hospitals, zoos and researchers. The owners of such animals are all concerned with providing a humane death.

Euthanasia compositions containing barbiturates are on the market. These solutions are controlled by the U.S. Drug Enforcement Administration (DEA) because of the barbiturates which are Class II or Class III controlled substances. There is a need for compositions which are not controlled because of the record keeping involved in handling the barbiturate compositions.

The need to formulate a new euthanasia composition was prompted by problems with a euthanasia composition which was marketed under the name "T-61" and is no longer on the market. It is comprised of an anesthetic, gamma-hydroxybutramide; a local anesthetic, tetracaine; a muscle relaxant, mebezonium; and a solvent, dimethylformamide. The composition of this solution contains as solids, 78% gamma-hydroxybutramide; 2% tetracaine; and 20% mebezonium, and as liquids a mixture of 60% dimethylformamide and 40% water. The solution contained 25.5% total solids and the solution has a syrup-like consistency and is injectable with a 22 gauge syringe.

A component of T-61 was causing adverse side effects when the product was rapidly injected intravenously. The physiological and pharmacological effects of each component of the euthanasia solution, T-61 were investigated. The anesthetic, gamma-hydroxybutramide, appeared to be an effective lethal drug at the recommended dose for T-61 (62 mg/kg). Its onset of action occurred within 15 to 25 seconds and has a smooth, calm induction with 47% ethanol used as a vehicle. Mebezonium, the neuromuscular blocking agent included in T-61 was found to be effective at the concentration contained in T-61. The equi-effective dose of mebezonium is about 3 mg/kg and at the volume recommended for euthanasia with T-61, the dose of the muscle relaxant is 15 mg/kg IV. The onset of effect at the equi-effective dose is approximately 75 seconds.

Tetracaine hydrochloride (5 mg/ml; 1.5 mg/kg) appeared to be responsible for bizarre behavioral effects when T-61 was given rapidly. This is a high dosage. This response, e.g., stiffening of the forelimbs, opisthotonos, and an apparent uneasy appearance was reproduced when tetracaine was given alone at the dose contained in T-61. This undesirable effect is most likely due to the direct stimulatory effects of tetracaine on the central nervous system. Tetracaine hydrochloride was recommended to be given slowly. In practice it was given rapidly and produced the undesired behavioral response. The euthanasia solutions approved by the FDA now for marketing do not allow a slow rate of injection since this is unpractical in use.

Dimethylformamide (DMF) is the solvent used in T-61 to keep embutramide in solution. This produces a thick solution. DMF is used at a 60% by volume in water concentration in T-61 and appears to have a local irritating effect at the site of injection. It also appears to have a central stimulating effect which is observed within the first 15 seconds following injection. This is then followed by a period of sedation lasting 15 to 30 minutes in some animals when given alone. It does not appear to alter the onset of anesthesia induced by embutramide nor contribute to the lethal effects of the anesthetic. The 60% concentration of DMF is too high and is most likely responsible for the discomfort induced when T-61 is given rapidly.

An additional problem with the T-61 composition is the appearance of a noticeable heart beat which persists during the euthanasia procedure. Although this activity of the heart is ineffective in perfusing body tissues, it nevertheless is visible in thin chested dogs or small animals and usually persists for many minutes. This is not esthetically pleasing to the owner nor to people performing this task who are not familiar with the time course or lethal effects of hypoxia.

There was thus a need for an improved euthanasia solution. Gamma-hydroxybutramide is not included on the list of drugs controlled by the Federal Drug Enforcement Agency. In addition, it has a rapid onset of action causing almost immediate anesthesia and cessation of breathing. The problem then was to provide an effective formulation which overcomes the problems of the prior art with T-61.

The lethal effects on the heart of chloroquine or quinacrine, which are antimalarial drugs in human beings, have been recognized. So far as is known, there has been no attempt to provide useful euthanasia formulations with these drugs.

In injectable formulations, the effects of potassium on the heart is known (Tona, Lutete, et al., European Journal of Pharmacology 178:293-301 (1990)). This can be seen in Mudge, G. H. Potassium section VII, Water, Salts and Ions. In *The Pharm. Basis of Therapeutics*, Goodman and and Gilman, Eds., MacMillan Publishing Co., New York, 1985, pp 866-874.

OBJECTS

It is therefore an object of the present invention to provide improved euthanasia compositions which rapidly eliminate the presence of a noticeable heart beat and the stiffening encountered with T-61. It is further an object to reduce or eliminate agonal breathing during the procedure. Further still it is an object of the present invention to provide compositions which are relatively inexpensive and which do not contain any DEA controlled substances. These and other objects will become increasingly apparent by reference to the following description.

GENERAL DESCRIPTION

The present invention relates to a method for providing euthanasia in a mammal which comprises introducing into the heart of the mammal an aqueous solution comprising in admixture a cardiotoxic compound selected from the group consisting of a quinacrine salt and a chloroquine salt in a cardiotoxic amount and a water solubilized gamma-hydroxybutramide in a lethally anesthetic amount, wherein euthanasia occurs in the mammal.

Further, the present invention particularly relates to a method for providing euthanasia in a mammal which comprises introducing into the heart of the mammal an effective amount of a mixture of gamma-hydroxybutramide dissolved in a water miscible liquid solubilizing agent; a water soluble chloroquine salt; and a water soluble inorganic salt selected from an alkali metal salt and alkaline earth metal salt other than a sodium salt in an aqueous solution so that the mammal is euthanasized within five (5) minutes.

The present invention also relates to a composition for providing euthanasia in a mammal which comprises in admixture in an injectable aqueous solution a cardiotoxic compound selected from the group consisting of a quinacrine salt and a chloroquine salt; and gamma-hydroxybutramide, wherein the solution contains a ratio of gamma-hydroxybutramide to chloroquine of between about 3 to 1 and 6 to 1 in an amount sufficient to produce euthanasia.

Finally the present invention relates to a composition for providing euthanasia in a mammal which comprises in admixture an aqueous solution, gamma-hydroxybutramide dissolved in a water immiscible liquid solubilizing agent; a water soluble chloroquine salt; and a water soluble inorganic salt selected from an alkali metal salt and an alkaline earth metal salt other than sodium chloride, wherein the solution contains a ratio of gamma-hydroxybutramide to chloroquine of between about 3 to 1 and 6 to 1 and a ratio of gamma-hydroxybutramide to salt of between about 0.01 to 0.02 and wherein the solution produces euthanasia.

The preferred compositions include as solids alone between about 70 to 80 percent by weight of the gamma-hydroxybutramide, 15 to 25 percent by weight of the chloroquine salt and preferably between 0.8 and 2.0% by weight of the water soluble salt. The composition preferably contains as liquids a mixture of about 40% to 60% by weight water and 40 to 60% by weight solubilizing agent, preferably ethanol or denatured alcohol in an amount sufficient to dissolve the solids. The solids are preferably between about 20 to 30 percent by weight of the solution. Within these ranges the lethal dosage of the composition as an aqueous solution is injected into the animal is preferably between about 0.15 and 0.35 ml per kg of body weight. In general, if too little of the composition is given the time to produce death is prolonged. If too much of the composition is given, unwanted side effects can be observed.

The preferred pH of the solution is between about 4.5 and 7.2 which is compatible with blood pH. Sodium bicarbonate can be used as buffer to provide a pH between about 6 and 7. Other buffers are for instance acetate, phosphate, MOPS, HEPES, TRIS and the like.

Preferably the inorganic salt is potassium chloride. This salt has a known cardiotoxic activity as discussed above. Other salts are magnesium, manganese, cobalt and cadmium.

The gamma-hydroxybutramide is preferably solubilized in a lower alkanol containing 1 to 3 carbon atoms. Most preferably ethanol is used which appears to be the least irritating locally at the site of injection. Denatured alcohol can be used since it is less expensive. Other carrier solutions can be used.

The water used for the formulation should be free of contamination and essentially sterile. The formulation is usually in injectable form.

In certain cases it may be desirable to package the solution in a form for multiple injection by semi-automatic syringe. The solution can be spray injected or injected through a needle.

In the preferred method between about 35 and 75 mg of gamma-hydroxybutramide, 5 and 18 mg of cardiotoxic compound and preferably between about 0.1 and 3 mg of inorganic water soluble salt per kg of body weight of the mammal is used to produce death in the mammal. Preferably the composition is formulated so that it can be used at a dosage between about 0.15 and 0.35 ml per kg of body weight of the mammal for ease of administration.

Gamma-hydroxybutramide is not water soluble and consequently ethanol was selected as the preferred solvent. Therefore, it was necessary to first put the gamma-hydroxybutramide into solution with ethanol and then combine it with chloroquine dissolved in water. Chloroquine and potassium are water soluble. The sodium bicarbonate was added to the solution as a buffer to a more neutral pH.

Agonal breathing was found to be a problem if death occurred too rapidly. The dose of each component can be changed slightly so that death occurs in 2.5 to 4 minutes instead of 1 to 2 minutes to reduce this problem.

SPECIFIC DESCRIPTION

Three different concentrations of gamma-hydroxybutramide and chloroquine given at volume doses of 0.30 and 0.35 ml/kg to make a total of six solutions were evaluated. By varying the concentrations of gamma-hydroxybutramide and chloroquine, the most efficacious mixture of these compounds and dose to achieve rapid euthanasia and to eliminate the side effect of agonal breathing were determined.

When embutramide and chloroquine stock solutions are mixed according to the "recipe," the final volume of both the chloroquine and embutramide is greater than the amount of liquid added. For example, when 10 ml of alcohol is added to dry embutramide, the final volume after the dry chemical is dissolved in the alcohol is approximately 14.5 ml. Chloroquine has a final volume after being dissolved in 10 ml of water of approximately 11.2 ml. Calculations are the actual mg/kg dosages based on the final volume of each component after dissolving into the stock solution.

Examples 1 to 12

A stock solution of 90% ethanol as the solvent for gamma-hydroxybutramide was used. The final concentration of ethanol in the mixtures tested was 45%. Additionally, sodium bicarbonate (75 mg/ml), was added to the mixtures to buffer them to a pH of 6.3 to 6.8. The solutions tested are listed in Table 1 and the mg/kg dose of each component in the solutions are presented in Table 2.

TABLE 1

| SOLUTIONS |
|---|
| STOCK SOLUTIONS |
| A. 4 grams embutramide in 10 ml 90% ETOH |
| B. 5 grams embutramide in 10 ml 90% ETOH |
| C. 6 grams embutramide in 10 ml 90% ETOH |
| D. 2 grams chloroquine diphosphate in 10 ml of H$_2$O |
| E. 3 grams chloroquine diphosphate in 10 ml of H$_2$O |
| F. 100 mg KCl in 5 ml of sodium bicarbonate (75 mg/ml) + 5 ml H$_2$O |
| MIXTURES |
| 1. A + .5E + .5F |

TABLE 1-continued

| SOLUTIONS | |
|---|---|
| 2. | B + .5E + .5F |
| 3. | C + .5E + .5F |
| 4. | A + .5D + .5F |
| 5. | B + .5D + .5F |
| 6. | C + .5D + .5F |

TABLE 2

MG/KG DOSAGES 0.30 ml/kg dose

| SOLUTION* | GAMMA HYDROXY-BUTRAMIDE | CHLOROQUINE DI-PHOSPHATE | KCL | NaHCO3 |
|---|---|---|---|---|
| 1 | 45.1 | 18.5 | 0.75 | 5.63 |
| 2 | 52.1 | 18.5 | 0.75 | 5.63 |
| 3 | 61.2 | 18.5 | 0.75 | 5.63 |
| 4 | 45.1 | 12.9 | 0.75 | 5.63 |
| 5 | 52.1 | 12.9 | 0.75 | 5.63 |
| 6 | 61.2 | 12.9 | 0.75 | 5.63 |

0.35 ml/kg dose

| SOLUTION* | GAMMA HYDROXY-BUTRAMIDE | CHLOROQUINE | KCL | NaHCO3 |
|---|---|---|---|---|
| 7 | 52.6 | 21.5 | 0.88 | 6.56 |
| 8 | 60.8 | 21.5 | 0.88 | 6.56 |
| 9 | 71.4 | 21.5 | 0.88 | 6.56 |
| 10 | 52.6 | 15.1 | 0.88 | 6.56 |
| 11 | 60.8 | 15.1 | 0.88 | 6.56 |
| 12 | 71.4 | 15.1 | 0.88 | 6.56 |

*amounts are in mg per kg of solution

All dogs had an IV catheter placed and a control injection of sterile water given at the same volume of injection as the test drug. The solutions were administered in a randomized blinded manner. Five dogs were tested with each solution at volume doses of 0.30 and 0.35 ml/kg. Scoring criteria are listed in Table 3.

TABLE 3

SCORING

1. Smooth induction, no reaction to the injection. death occurs within 3 minutes.
2. Smooth induction, no reaction to the injection, heart beat is visible more than 3 minutes but less than 5 minutes.
3. Animal shows a reaction to the injection; heart beat visible for less than 3 minutes.
4. Animal shows a reaction to the injection. AND/OR heart beat is visible more than 3 minutes.
5. Unsatisfactory euthanasia: agonal breaths*, bad reaction AND/OR animal does not die and must be given another drug for euthanasia after 5 minutes.

RESULTS

The results from these studies are listed in Tables 4 and 5.

TABLE 4

RESULTS 0.30 ML/KG DOSE

| | SOLUTION | | | | | |
|---|---|---|---|---|---|---|
| | #1 | #2 | #3 | #4 | #5 | #6 |
| | SCORES | | | | | |
| | 1 | 2 | 5 | 2 | 4 | 2 |
| | 5 | 5 | 5 | 4 | 1 | 5 |
| | 5 | 5 | 5 | 5 | 5 | 1 |
| | 5 | 5 | 1 | 2 | 4 | 5 |
| | 1 | 1 | 5 | 1 | 5 | 5 |
| MEAN SCORE | 3.4 | 3.6 | 4.2 | 2.8 | 3.8 | 3.6 |
| TIME OF DEATH (Minutes) | | | | | | |

TABLE 4-continued

RESULTS 0.30 ML/KG DOSE

| | SOLUTION | | | | | |
|---|---|---|---|---|---|---|
| | #1 | #2 | #3 | #4 | #5 | #6 |
| | 2:45 | 4:50 | 2:30 | 3:15 | 4:50 | 3:15 |
| | 2:00 | 2:30 | 2:10 | 6:30 | 2:55 | 2:00 |
| | 2:30 | 2:50 | 2:45 | >5:00 | 3:15 | 2.50 |
| | 1:00 | 2:00 | 3:00 | 4:15 | 5:00 | 1:00 |
| | 3:00 | 1:50 | 1:00 | 2:30 | 1:30 | 3:30 |
| MEAN | 2:18 | 2:48 | 2:15 | 4:18 | 3:30 | 2:30 |
| INCIDENCE OF AGONAL BREATHING | | | | | | |
| | 60% | 60% | 80% | 0% | 40% | 40% |

TABLE 5

RESULTS 0.35 ML/KG DOSE

| | SOLUTION | | | | | |
|---|---|---|---|---|---|---|
| | #7 | #8 | #9 | #10 | #11 | #12 |
| | 3 | 5 | 1 | 1 | 5 | 5 |
| | 2 | 1 | 1 | 5 | 1 | 1 |
| | 1 | 2 | 5 | 5 | 1 | 1 |
| | 5 | 1 | 5 | 1 | 5 | 1 |
| | 5 | 5 | 5 | 1 | 2 | 1 |
| MEAN SCORE | 3.2 | 2.8 | 3.4 | 2.6 | 2.8 | 1.8 |
| TIME OF DEATH (Minutes) | | | | | | |
| | 1:00 | 2:00 | 1:00 | 2:45 | 3:30 | 2:00 |
| | 4:15 | 1:00 | 1:00 | 2:00 | 2:30 | 1:00 |
| | 2:30 | 3:23 | 2:00 | 2:30 | 2:48 | 2:45 |
| | 2:00 | 3:00 | 2:30 | 2:00 | 2:30 | 2:45 |
| | 1:00 | 1:00 | 2:30 | 2:30 | 3:45 | 2:5 |
| MEAN | 2:12 | 2:06 | 1:48 | 2:24 | 3:00 | 2:18 |
| INCIDENCE OF AGONAL BREATHING | | | | | | |
| | 40% | 40% | 60% | 40% | 40% | 20% |

The best solution tested was number 12 at a volume dose of 0.35 ml/kg: gamma-hydroxybutramide (71.4 mg/kg), chloroquine (15.5 mg/kg), KCL (0.88 mg/kg), and pH 6.56). The solution had the best overall score of 1.8 as well as only a 20% incidence of agonal breathing. This solution did not induce the shortest time of death, however, with a mean time of death of 2.3 minutes, it is well within the preferred goal of death occurring in less than 3 minutes. When agonal breathing was observed, it consistently occurred at 2 minutes with the heart beat stopping within a few seconds thereafter.

As can be seen from Example 1, even with these modifications in the mixture of gamma-hydroxybutramide, chloroquine, and potassium, agonal breathing was not eliminated. It is apparent from these studies that time of death is a factor associated with agonal breathing. Also, chloroquine may be responsible for a faster onset of death, but may have caused the increased incidence of agonal breathing as well. If one compares number 9 to number 12 at the 0.35 ml/kg dose, the only major difference is that the chloroquine dose is the highest (21.5 mg/kg) and the time of death is 30 seconds faster. This is also evident at the 0.30 mg/kg dose where chloroquine is highest in solution numbers 1, 2 and 3 and the time of death tends to be shorter than numbers 4, 5 and 6. It is interesting to note that solution number 4, which is the low concentration of both chloroquine and gamma-hydroxybutramide, had a 0% incidence of agonal breathing at the 0.30 mg/kg dose which indicates that gamma-hydroxybutramide may play a role as well. Solution number 4 had the best overall score at the 0.30 mg/kg dose, but the longest time of death for all solutions at both dosages at a mean of 4.3 minutes. Thus a composition can be produced which will not induce any possibility of agonal breathing with humane death occurring in less than 3 minutes or a solution can be produced that produces humane death without agonal breathing in 3 to 6 minutes, but might have a visible heart beat for part of that time.

Usually as little ethanol and water is used as is necessary to provide a solution. This produces a formulation as shown in Table 6:

TABLE 6

|  | 0.25 ml/kg | 0.3 ml/kg |
|---|---|---|
| 204.1–206.9 mg/ml gamma-hydroxybutramide | 51 mg | 61 mg |
| 43.1–44.7 mg/ml chloroquine | 10.8 mg | 12.9 mg |
| 2.5 mg/ml potassium chloride | 0.6 mg | 0.8 mg |
| 9.4 mg/ml sodium bicarbonate | 2.4 mg | 2.8 mg |

It is intended that the foregoing description be only illustrative of the present invention and that the invention be limited only by the hereinafter appended claims.

We claim:

1. A method for providing euthanasia in a mammal which comprises introducing by injection into the mammal an aqueous solution comprising in admixture of cardiotoxic compound selected from the group consisting of a quinacrine salt and a chloroquine salt in a cardiotoxic amount and a water solubilized gamma-hydroxybutramide in a lethally anesthetic amount, wherein euthanasia occurs in the mammal.

2. The method of claim 1 wherein the chloroquine salt is chloroquine diphosphate and the quinacrine salt is quinacrine hydrochloride.

3. A method for providing euthanasia in a mammal which comprises:
   introducing by injection into the mammal an effective amount of a mixture of gamma-hydroxybutramide dissolved in a water miscible liquid solubilizing agent;
   a water soluble chloroquine salt; and
   a water soluble inorganic salt selected from an alkali metal salt and alkaline earth metal salt other than a sodium salt in an aqueous solution so that the mammal is euthanatized within five (5) minutes.

4. The method of claim 3 wherein the chloroquine salt is chloroquine diphosphate.

5. The method of claim 3 wherein the liquid solublizing agent is a lower alkanol containing 1 to 3 carbon atoms.

6. The method of claim 3 wherein the water soluble inorganic salt is potassium chloride.

7. The method of claim 3 wherein the mixture is formulated in a single unit dosage form.

8. The method of claim 3 wherein sodium bicarbonate as a buffer is provided in the solution and the pH of the solution is between about pH 4.5 and 7.2.

9. The method of claim 3 wherein the liquid solubilizing agent is ethanol or denatured ethanol, the chloroquine salt is chloroquine diphosphate, and the water soluble inorganic salt is potassium chloride.

10. The method of claim 9 wherein the solution contains a ratio of gamma-hydroxybutramide to chloroquine of between 3 to 1 and 6 to 1 and gamma-hydroxybutramide to salt of between about 100 to 1 and 200 to 1.

11. The method of claim 10 wherein the solution is introduced into the blood stream of the mammal at a dosage between about 0.15 and 0.35 ml per kg of body weight of the mammal.

12. The method of claim 3 wherein the solution is in an injectable form and contains between about 35 and 75 mg of gamma-hydroxybutramide; between about 5 and 18 mg of chloroquine salt and between about 0.1 and 3 mg of water soluble inorganic salt per kg of body weight of the mammal which is administered to the mammal in the solution as a single dosage unit.

13. The method of claim 3 wherein the mammal is a domestic animal.

14. The method of claim 3 wherein the mammal is a dog.

15. A composition for providing euthanasia in a mammal which comprises in admixture in an injectable aqueous solution
   (a) a cardiotoxic compound selected from the group consisting of a quinacrine salt and a chloroquine salt; and
   (b) gamma-hydroxybutramide, wherein the solution contains a ratio of gamma-hydroxybutramide to chloroquine of between about 3 to 1 and 6 to 1 in an amount sufficient to produce euthanasia.

16. The composition of claim 15 wherein the chloroquine salt is chloroquine diphosphate and the quinacrine salt is quinamine hydrochloride.

17. The composition of claim 16 in a multiple injection form for dispensing in a syringe.

18. The composition of claim 15 wherein a dosage provides between about 0.15 and 0.35 ml of the composition per kg of body weight of the mammal to produce euthanasia.

19. The composition of claim 15 wherein the solution contains a ratio of gamma-hydroxybutramide to chloroquine of between 3 to 1 and 6 to 1 and gamma-hydroxybutramide to salt of between about 100 to 1 and 200 to 1.

20. The composition of claim 19 in a single unit dosage form containing between about 0.15 and 0.35 ml per kg of body weight of the mammal.

21. The composition of claim 19 wherein the aqueous solubilizing agent is selected from the group consisting of ethanol and denatured ethanol, the chloroquine salt is chloroquine diphosphate, the water soluble inorganic salt is potassium chloride.

22. The composition of claim 21 wherein sodium bicarbonate is provided in the solution as a buffer and the pH of the solution is between about pH 4.5 and 7.2

23. The composition of claim 21 in a single unit dosage form.

* * * * *

UNITED STATES PATENT AND TRADEMARK OFFICE
CERTIFICATE OF CORRECTION

PATENT NO. : 5,281,611
DATED : Janyary 25, 1994
INVENTOR(S) : Donald C. Sawyer, Theodore M. Brody, Marlee A. Langham It is certified that error appears in the above-indentified patent and that said Letters Patent is hereby corrected as shown below:

Column 7, line 23, "admixture of" should read --admixture a--.

Signed and Sealed this

Thirty-first Day of May, 1994

Attest:

BRUCE LEHMAN

*Attesting Officer*   *Commissioner of Patents and Trademarks*